(12) United States Patent
Inaba et al.

(10) Patent No.: US 9,874,416 B2
(45) Date of Patent: Jan. 23, 2018

(54) COOLING DEVICE HAVING FUNCTION TO DETECT CLOGGING OF RADIATION FINS

(71) Applicant: FANUC CORPORATION, Yamanashi (JP)

(72) Inventors: Kiichi Inaba, Yamanashi (JP); Shigeki Hanyu, Yamanashi (JP); Tomokazu Yoshida, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 0 days.

(21) Appl. No.: 15/279,758

(22) Filed: Sep. 29, 2016

(65) Prior Publication Data
US 2017/0097199 A1    Apr. 6, 2017

(30) Foreign Application Priority Data
Oct. 2, 2015    (JP) .................................. 2015-196636

(51) Int. Cl.
*B60H 1/00*    (2006.01)
*F28F 27/00*    (2006.01)
(Continued)

(52) U.S. Cl.
CPC ............... *F28F 27/00* (2013.01); *F28F 3/02* (2013.01); *F28F 19/00* (2013.01); *G01N 27/20* (2013.01); *H01L 23/36* (2013.01); *F28F 2250/08* (2013.01)

(58) Field of Classification Search
CPC .... F28F 27/00; F28F 3/02; F28F 19/00; F28F 2250/08; G01N 27/20; H01L 23/36
(Continued)

(56) References Cited

U.S. PATENT DOCUMENTS

2005/0247194 A1* 11/2005 Kang ................. B01D 46/0086
  95/19
2009/0051882 A1*  2/2009 Yoshimura ............. G03B 21/16
  353/57
(Continued)

FOREIGN PATENT DOCUMENTS

JP    201498523 A    5/2014
JP    2014165421 A   9/2014

OTHER PUBLICATIONS

English Abstract and Machine Translation for Japanese Publication No. 2014-098523 A, published May 29, 2014, 19 pgs.
(Continued)

*Primary Examiner* — Justin Jonaitis
(74) *Attorney, Agent, or Firm* — Fredrikson & Byron, P.A.

(57) ABSTRACT

A cooling device includes an electrode unit which is arranged in a space between adjacent radiation fins and which is electrically insulated from the radiation fins, and a power supply source which applies a voltage between a heat radiation structure and the electrode unit. The cooling device is further provided with an insulation resistance detection unit which calculates an insulation resistance between the heat radiation structure and the electrode unit, and a comparison unit which compares the insulation resistance calculated by the insulation resistance detection unit with a predetermined threshold, wherein, as a result of the comparison of the calculated insulation resistance and the predetermined threshold by the comparison unit, when the calculated insulation resistance is lower than the predetermined threshold, the cooling device is adapted to judge that the radiation fins have clogged.

2 Claims, 5 Drawing Sheets

(51) Int. Cl.
  *F28F 3/02* (2006.01)
  *F28F 19/00* (2006.01)
  *G01N 27/20* (2006.01)
  *H01L 23/36* (2006.01)

(58) Field of Classification Search
  USPC ........................................................ 165/11.1
  See application file for complete search history.

(56) References Cited

U.S. PATENT DOCUMENTS

2009/0299531 A1\* 12/2009 Kitamura ........... G05B 23/0235
                                                            700/275
2010/0294134 A1\* 11/2010 Yokomizo .......... B01D 46/0065
                                                            96/405
2015/0144074 A1\* 5/2015 Fujimoto .............. F28G 15/003
                                                            122/14.21

OTHER PUBLICATIONS

English Abstract and Machine Translation for Japanese Publication No. 2014-165421 A, published Sep. 8, 2014, 7 pgs.

\* cited by examiner

WHEN NO CLOGGING OF DUST-PROOF FILTER OCCURS

FIG. 5B

WHEN CLOGGING OF DUST-PROOF FILTER OCCURS

DETECTION OF OCCURRENCE
OF CLOGGING

FIG. 5C

WHEN AMOUNT OF HEAT GENERATED BY HEAT GENERATING
BODY INCREASES DUE TO INCREASE OF LOAD THEREOF
WITHOUT OCCURRENCE OF CLOGGING OF DUST-PROOF FILTER

ERRONEOUS DETECTION OF
OCCURRENCE OF CLOGGING

FIG. 6

COOLING DEVICE HAVING FUNCTION TO DETECT CLOGGING OF RADIATION FINS

BACKGROUND OF THE INVENTION

1. Field of the Invention

The present invention relates to a cooling device comprising a cooling fan and radiation fins and having a function of detecting that the radiation fins have clogged.

2. Description of the Related Art

There are conventionally known cooling devices having a plurality of radiation fins which are sequentially arranged at predetermined distances on a heat generating body wherein an air flow which flows in spaces between the adjacent radiation fins is generated by a cooling fan to cool the heat generating body. Among such conventional cooling devices, some are provided with a clogging detection function wherein the temperature of the heat generating body is monitored by a temperature sensor and when the temperature of the heat generating body exceeds a predetermined value, it is judged that the radiation fins have clogged.

A cooling device provided with such a clogging detection function is disclosed in Japanese Patent Application Laid-open No. 2014-165421 or Japanese Patent Application Laid-open No. 2014-098523, etc.

Figure 4:
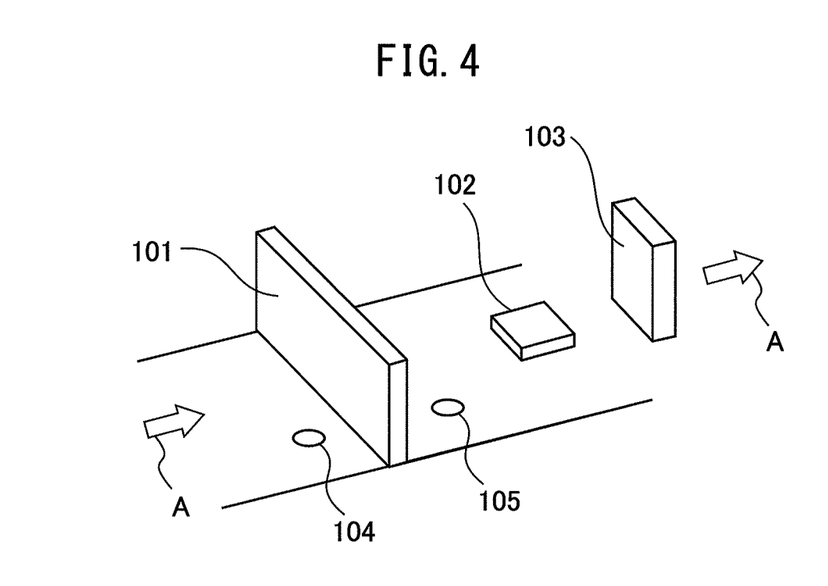
FIG. 4 is a view schematically showing a known cooling device disclosed in Japanese Patent Application Laid-open No. 2014-165421.

FIG. 4 schematically illustrates a conventional cooling device (which will be hereinafter referred to as the "cooling device of Prior Art 1") disclosed in Japanese Patent Application Laid-open No. 2014-165421.

As can be seen in FIG. 4, in the cooling device of Prior Art 1, a dust-proof filter 101, a heat generating body 102, and a cooling fan 103 are sequentially arranged along the flow direction "A" of the air flow generated by the cooling fan 103. A first temperature sensor 104 is arranged on the upstream side of the dust-proof filter 101 in terms of the air flow direction "A", and a second temperature sensor 105 is arranged on the downstream side of the dust-proof filter 101 in terms of the air flow direction "A".

Figure 5A:
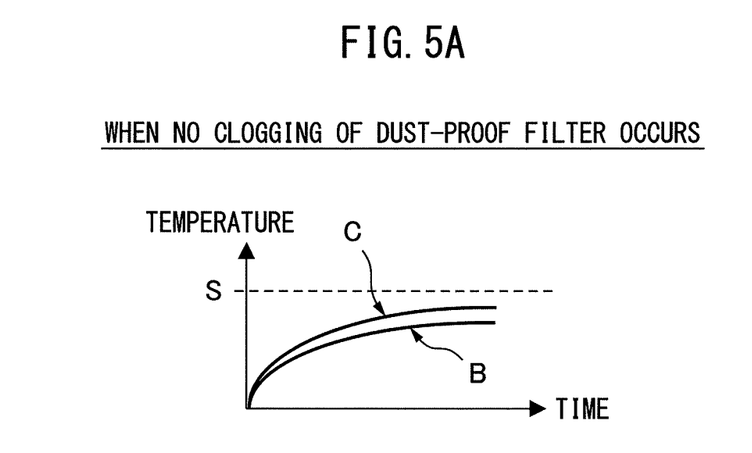
FIG. 5A is a diagram showing temporary changes of the detection temperatures of temperature sensors when no clogging of a dust-proof filter occurs.
Figure 5B:
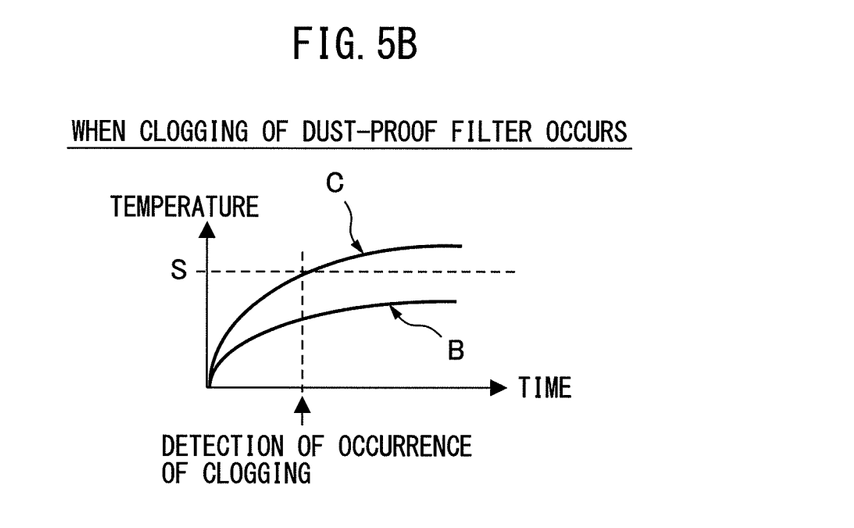
FIG. 5B is a diagram showing temporary changes of the detection temperatures of temperature sensors when clogging of a dust-proof filter occurs.
Figure 5C:
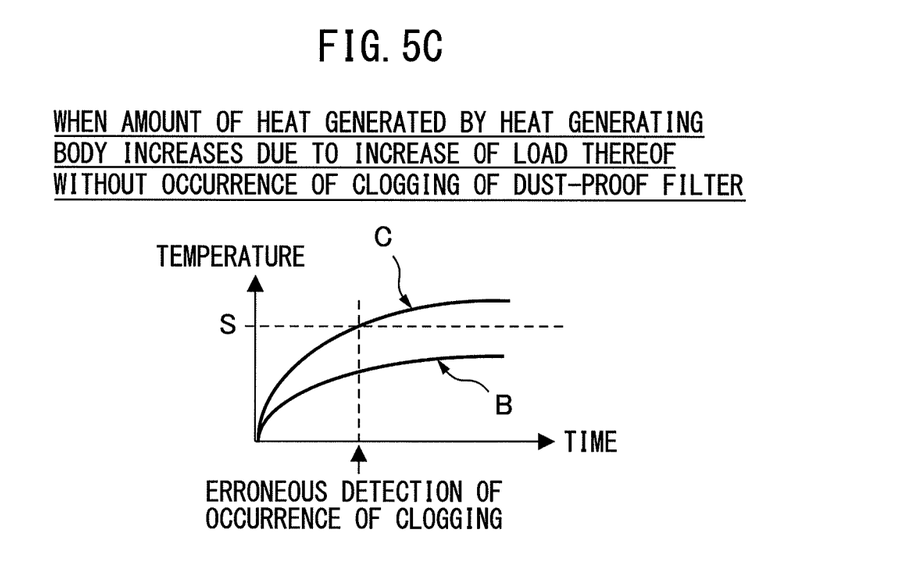
FIG. 5C is a diagram showing temporary changes of the detection temperatures of temperature sensors when a heat generating body generates heat due to an increase of the load thereof even if no clogging of a dust-proof filter occurs.

FIGS. 5A to 5C are diagrams showing changes over time of the temperatures detected by the first and second temperature sensors 104 and 105. In each of FIGS. 5A to 5C, the curved line indicated by B represents a temperature change over time, detected by the first temperature sensor 104 and the curved line indicated by C represents a temperature change over time, detected by the second temperature sensor 105. In particular, FIG. 5A shows temperature changes over time, detected by the first and second temperature sensors 104 and 105 when no clogging of the dust-proof filter 101 occurs and FIG. 5B shows temperature changes over time, detected by the first and second temperature sensors 104 and 105 when the dust-proof filter 101 has clogged.

When no clogging of the dust-proof filter 101 occurs, as can be seen in FIG. 5A, the temperatures detected by the first and second temperature sensors 104 and 105 do not exceed a predetermined temperature threshold S. However, once the dust-proof filter 101 clogs, as can be seen in FIG. 5B, the temperature detected by the second temperature sensor 105 exceeds the predetermined temperature threshold S. Thus, the cooling device of Prior Art 1 is adapted to judge that the dust-proof filter 101 has clogged when the detected temperature of the second temperature sensor 105 exceeds the temperature threshold S.

Figure 6:
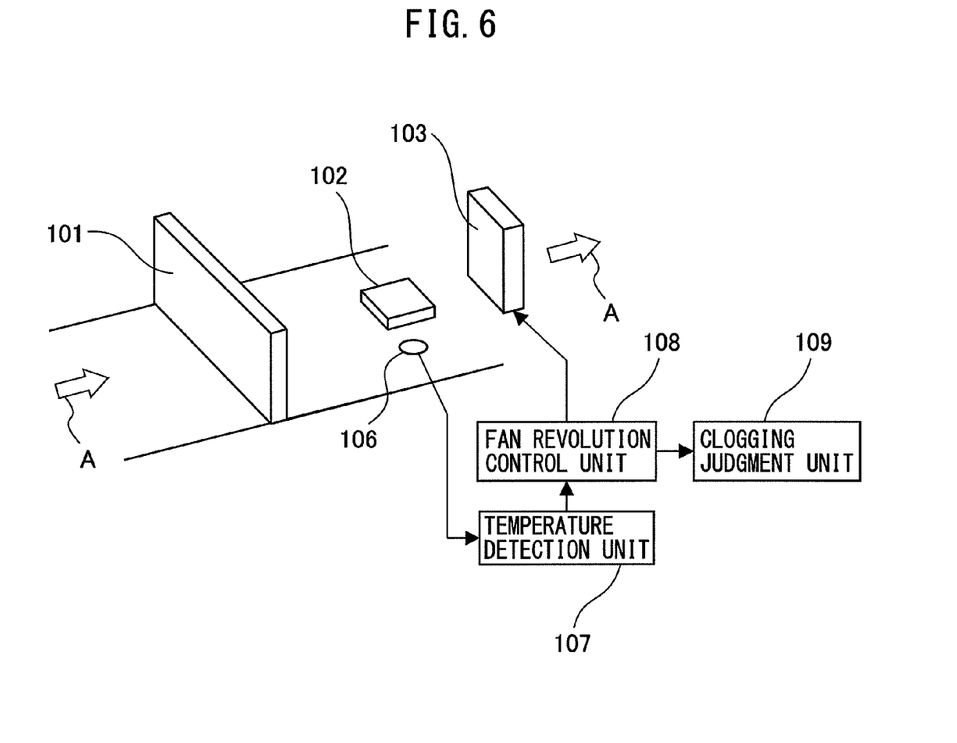
FIG. 6 is a view schematically showing a known cooling device disclosed in Japanese Patent Application Laid-open No. 2014-098523.

FIG. 6 schematically shows a conventional cooling device (which will be referred to hereinafter as to the "cooling device of Prior Art 2") disclosed in Japanese Patent Application Laid-open No. 2014-098523. The components corresponding to those of the cooling device of Prior Art 1 mentioned above are assigned the same reference numerals.

As shown in FIG. 6, in the cooling device of Prior Art 2, a dust-proof filter 101, a heat generating body 102 and a cooling fan 103 are sequentially arranged in the flow direction "A" of the air flow generated by the cooling fan 103. As can be seen in FIG. 6, a temperature sensor 106 is arranged in the vicinity of the heat generating body 102 to detect the ambient temperature of the heat generating body 102.

Furthermore, the cooling device of Prior Art 2 is provided with a temperature detection unit 107, a fan revolution control unit 108 for controlling the number of revolutions of the fan, and a clogging judgment unit 109, as can be seen in FIG. 6.

The temperature detection unit 107 monitors a temporary change of the temperature detected by the temperature sensor 106. The fan revolution control unit 108 increases and monitors the number of revolutions of the cooling fan 103 in accordance with the ambient temperature of the heat generating body 102 detected by the temperature sensor 106. The clogging judgment unit 109 is adapted to judge that the dust-proof filter 101 has clogged when the monitored number of revolutions of the cooling fan 103 exceeds a predetermined value.

However, in the aforementioned cooling device of Prior Art 1, even if no clogging of the dust-proof filter 101 occurs, when the heat generating body 102 generates heat due to an increase of the load thereof, the detection temperature of the second temperature sensor 105 may exceed the predetermined temperature threshold S as can be seen in FIG. 5C. In this case, it is erroneously judged that the dust-proof filter 101 has clogged. Consequently, the aforementioned cooling device of Prior Art 1 has a problem that clogging of the dust-proof filter 101 cannot be correctly detected.

The same problem may arise in the cooling device of Prior Art 2. Namely, in the cooling device of Prior Art 2 mentioned above, even if no clogging of the dust-proof filter 101 occurs, when the heat generating body 102 generates heat due to an increase of the load thereof, the number of revolutions of the cooling fan 103 may exceed a reference value in accordance with the ambient temperature of the heat generating body 102. In this case, it is erroneously judged that the dust-proof filter 101 has clogged. Consequently, the aforementioned cooling device of Prior Art 2 also has a problem that clogging of the dust-proof filter 101 cannot be correctly detected.

Moreover, a temperature change per unit time decreases as the thermal time constant of the cooling device increases in accordance with the coolability. Therefore, in the cooling device of Prior Art 1 and the cooling device of Prior Art 2 mentioned above, it may be impossible to correctly detect that the filter 101 has clogged without monitoring the temperature of the heat generating body 102 for a long time period.

SUMMARY OF THE INVENTION

The present invention provides a cooling device which can detect the occurrence of clogging correctly and within a short period of time without monitoring the temperature of the heat generating body.

According to the first aspect of the invention, there is provided a cooling device comprising: a heat radiation structure having a plurality of radiation fin portions to be arranged on a heat generating body; a cooling fan which generates an air flow which flows in a space between the radiation fin portions; an electrode unit which is provided in the space and which is electrically insulated from the radiation fin portions; a power supply source which applies a voltage between the heat radiation structure and the electrode unit; a voltage detection unit which detects a voltage applied between the heat radiation structure and the electrode unit; a current detection unit which detects a current which flows in a circuit formed by sequentially electrically connecting at least the power supply source, the electrode unit, and the heat radiation structure; an insulation resistance detection unit which calculates an insulation resistance between the heat radiation structure and the electrode unit based on the detection results of the voltage detection unit and the current detection unit; and a comparison unit which compares the insulation resistance calculated by the insulation resistance detection unit with a predetermined threshold, wherein, as a result of the comparison of the insulation resistance calculated by the insulation resistance detection unit and the predetermined threshold by the comparison unit, when the calculated insulation resistance is lower than the predetermined threshold, the cooling device is adapted to judge that the radiation fin portions have clogged.

According to the second aspect of the invention, the cooling device according to the first aspect of the invention further comprises a setting unit which sets the predetermined threshold, wherein the predetermined threshold set by the setting unit is rewritable.

BRIEF DESCRIPTION OF THE DRAWINGS

The aforementioned objects, features and advantageous effects and other objects, features and advantageous effects of the present invention will be more clearly understood from the detailed description of the representative embodiments of the invention illustrated in the accompanying drawings.

DETAILED DESCRIPTION

Embodiments of the present invention will be discussed below with reference to the drawings. In the drawings, the same components are assigned the same reference numerals. The components assigned the same reference numerals in different drawings have the same function. For easy understanding, the scale of each drawing has been appropriately changed.

Figure 1:
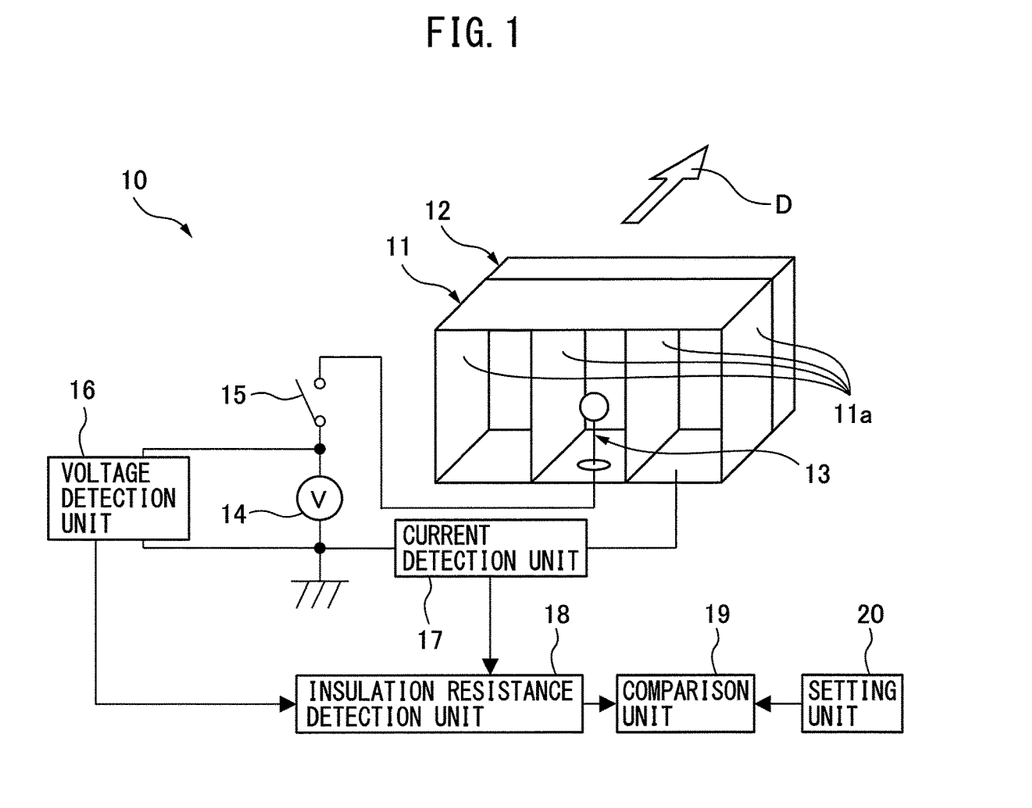
FIG. 1 is a block diagram showing the structure of a cooling device according to an embodiment of the present invention.

FIG. 1 is a block diagram showing the structure of a cooling device according to an embodiment of the present invention.

As can be seen in FIG. 1, a cooling device 10 of this embodiment is composed of a heat radiation structure 11 having a plurality of radiation fin portions 11a to be arranged on a heat generating body (not shown), and a cooling fan 12 which generates air flows flowing in spaces defined between the adjacent radiation fin portions 11a. The cooling fan 12 is, for example, a fan motor.

In the cooling device 10 of this embodiment, when the cooling fan 12 is operated, air flows in the spaces defined between the adjacent radiation fin portions 11a in a direction indicated by the arrow D in FIG. 1. Consequently, heat of the heat generating body (not shown) is transmitted to each radiation fin portion 11a which is in turn cooled by the air.

Moreover, as can be seen in FIG. 1, the cooling device 10 is provided with an electrode unit 13 which is arranged in a space defined between the adjacent radiation fin portions 11a and which is electrically insulated from each radiation fin portion 11a, and a power supply source 14 which applies a voltage between the electrode unit 13 and the heat radiation structure 11.

Furthermore, the cooling device 10 is provided with a switching unit 15 which is adapted to control ON/OFF of the application of voltage by the power supply source 14, a voltage detection unit 16 which detects a value of voltage applied between the electrode unit 13 and heat radiation structure 11, and a current detection unit 17 which detects a value of current flowing in a circuit formed by electrically and sequentially connecting the power supply source 14, the switching unit 15, the electrode unit 13, and the heat radiation structure 11. In addition, the cooling device 10 is provided with an insulation resistance detection unit 18 which calculates a value of insulation resistance between the heat radiation structure 11 and the electrode unit 13 based on the detection results of the voltage detection unit 16 and the current detection unit 17, a comparison unit 19 which compares the insulation resistance value calculated by the insulation resistance detection unit 18 with a predetermined threshold, and a setting unit 20 which sets the predetermined threshold.

As a result of comparison of the insulation resistance value calculated by the insulation resistance detection unit 18 with the predetermined threshold by the comparison unit 19, if the calculated insulation resistance value is below the predetermined threshold, the comparison unit 19 judges that the radiation fin portions 11a have clogged.

In the aforementioned setting unit 20, it is preferable that the insulation resistance value as the predetermined threshold is rewritable.

Figure 2:
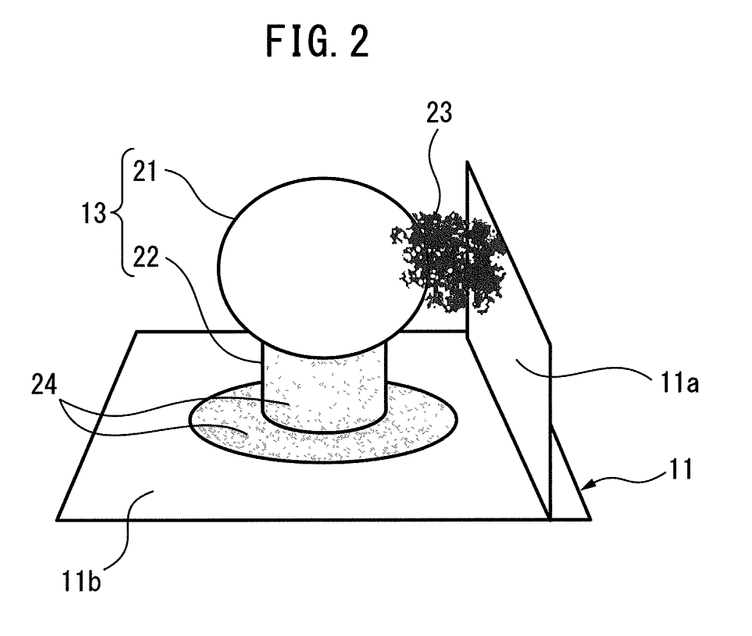
FIG. 2 is an enlarged perspective view of an electrode unit shown in FIG. 1, to illustrate how clogging is detected.
Figure 3:
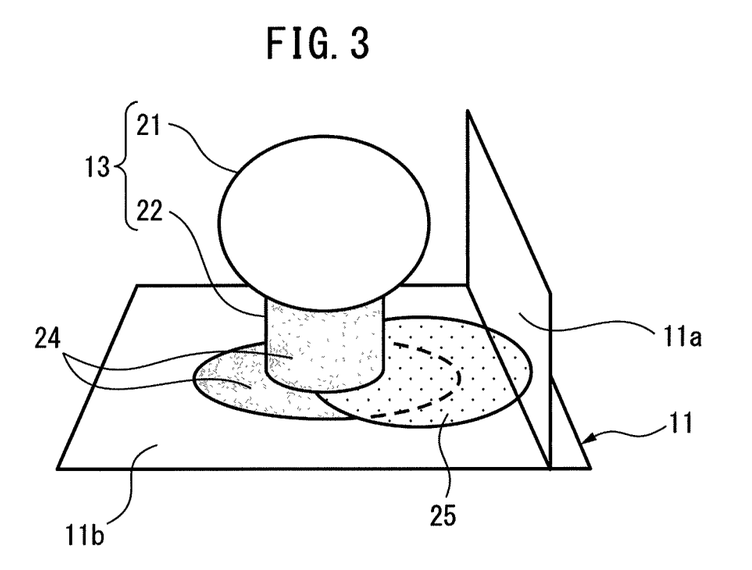
FIG. 3 is an enlarged perspective view of an electrode unit shown in FIG. 1, to explain the shape feature of the electrode unit.

FIG. 2 is an enlarged perspective view of the electrode unit 13 shown in FIG. 1, which is to explain how the clogging is detected. FIG. 3 is an enlarged perspective view of the electrode unit 13 shown in FIG. 1, which is to explain the shape feature of the electrode unit 13.

The electrode unit 13 is provided with a spherical electrode 21 and a support member 22 which supports the electrode 21 with respect to the heat radiation structure 11, as shown in FIG. 2. Specifically, the support member 22 extends to protrude from a horizontal plane 11b of the heat radiation structure 11. The electrode 21 is supported on the front end of the support member 22 so that the electrode 21 is located away from the fin portions 11a in the air.

Furthermore, the electrode 21 is electrically connected to the high voltage side (FIG. 1) of the power supply source 14 through the support member 22. The heat radiation structure 11 having the radiation fin portions 11a is electrically connected to the earth side (FIG. 1) of the power supply source 14. The heat radiation structure 11 and the support member 22 are electrically conductive, but the surface of the support member 22 is covered with an insulation material 24. Consequently, voltage can be applied only between the electrode 21 and the heat radiation structure 11.

With reference to FIGS. 1 and 2, when the switching unit 15 is turned ON, a voltage is applied from the power supply source 14 between the electrode 21 of the electrode unit 13 and the heat radiation structure 11 having the radiation fin portions 11a. The insulation resistance detection unit 18 calculates an insulation resistance (=voltage/current) between the heat radiation structure 11 and the electrode 21, on the basis of the voltage value detected by the voltage detection unit 16 and the current value detected by the current detection unit 17. When no clogging of the spaces between the adjacent fin portions 11a occurs, the insulation resistance between the heat radiation structure 11 and the electrode 21 becomes a very high value, e.g., a few hundred megohms (MΩ), since there are nothing in the space between the heat radiation structure 11 and the electrode 21.

However, as shown in FIG. 2, if impurities 23, such as fine particles in the air, metal waste, cutting liquid, or water enter the space between the heat radiation structure 11 and the electrode 21, the insulation resistance between the heat radiation structure 11 and the electrode 21 decreases to, for example, a few kilohms (KΩ).

As may be understood from the foregoing, in the cooling device 10 according to the illustrated embodiment, when the value of the insulation resistance between the heat radiation structure 11 and the electrode 21 becomes below a predetermined threshold, it is judged that the space between the adjacent radiation fin portions 11a has clogged.

This type of clogging judgment method is not a judgment method in which the occurrence of clogging is judged based on the temperature of the heat generating body or the heat radiation structure 11, and therefore the occurrence of clogging can be detected correctly and within a short period of time. Namely, according to the illustrated embodiment, unlike the aforementioned known cooling device of Prior Art 1 or Prior Art 2, there is no problem that if the heat generating body generates heat due to an increase of the load thereof, even if no clogging actually occurs, it may be erroneously judged that clogging has occurred. In addition, it is not necessary to monitor the temperature of the heat radiation structure 11 for a long period of time taking the thermal time constant of the heat radiation structure 11 into account.

Note that, in the illustrated embodiment, there is a case where liquid 25 such as cutting liquid or water is adhered to the horizontal surface 11b of the heat radiation structure 11, but no clogging occurs, as shown in FIG. 3. In this case, when the value of the insulation resistance between the heat radiation structure 11 and the electrode 21 becomes smaller than the predetermined threshold, due to the presence of the liquid 25, it is erroneously judged that clogging has occurred. To prevent this, as can be seen in FIGS. 2 and 3, the electrode 21 is supported in the air by the support member 22 which projects from the horizontal surface 11b of the heat radiation structure 11, and the surface of the support member 22 is covered by the insulation material 24.

In order to more reliably prevent the aforementioned erroneous judgment, preferably, not only the surface of the support member 22 but also the portion of the horizontal surface 11b of the heat radiation structure 11 surrounding the support member 22 are covered with the insulation material 24, as shown in FIGS. 2 and 3.

Moreover, in the aforementioned embodiment of the invention, the heat radiation structure 11 is made of an electrically conductive material. However, the heat radiation structure 11 may be made of a non-conductive material. In this case, it is preferable that an additional electrode be provided on the surface of the heat radiation structure 11 and an insulation resistance between the additional electrode and the electrode 21 be detected.

Although only one electrode unit 13 is provided in the space between the adjacent radiation fin portions 11a in the embodiment illustrated in FIG. 1, the number of the electrode units 13 is not limited to one in the present invention and two or more electrode units 13 may be provided. For example, a plurality of electrode units 13 may be intensively arranged in the vicinity of the portion of the heat radiation structure 11 where clogging tends to occur. Moreover, the shape of the electrode 21 of the electrode unit 13 is not limited to a specific shape but may be, for example, of a plate or rod.

Furthermore, regarding the predetermined threshold which is used to judge the decrease of the insulation resistance between the heat radiation structure 11 and the electrode unit 13, a plurality of thresholds are preferably provided. For example, a first threshold and a second threshold which is smaller than the first threshold are stored in the setting unit 20 as the predetermined thresholds. When the insulation resistance detected by the insulation resistance detection unit 18 decreases to a value smaller than the first threshold, a warning is preferably provided, and when it further decreases to a value smaller than the second threshold, an alarm sound is preferably issued.

Furthermore, regarding the voltage of the power supply source 14 to be applied between the heat radiation structure 11 and the electrode unit 13, a voltage of a DC linkage provided in an inverter system or a converter system used in a power supply for an instrument on which the cooling device 10 is mounted may be used. In this case, it is preferable that the detection operation of the insulation resistance be carried out during the stoppage of the inverter system or the converter system, so as to prevent the control operation of the inverter or converter from being influenced by the detection operation of the insulation resistance between the radiation structure 11 and the electrode unit 13.

If a plurality of cooling devices 10 are mounted on an instrument, the insulation resistance detected by the insulation resistance detection unit 18 of each of the cooling devices 10 is preferably transmitted or communicated to a numerical control device or a tablet terminal using communication means. As a result, it is possible to easily identify the cooling device 10 whose radiation fin portions 11a have clogged to thereby determine whether the heat radiation structure 11 thereof must be cleaned or replaced. Thus, the downtime due to maintenance of the cooling device 10 can be reduced.

Although the present invention has been discussed above with reference to the representative embodiments, it will be understood by a person skilled in the relevant art that the aforementioned modifications, a variety of other modifications, changes, omission, and addition can be made without departing from the scope of the present invention.

EFFECT OF THE INVENTION

According to the present invention, the occurrence of clogging is judged based on not the temperature of the heat generating body or the heat radiation structure, but a decrease of the insulation resistance between the heat radiation structure and the electrode unit, and therefore, the judgment can be performed correctly and within a short period of time. Namely, according to the present invention, unlike the aforementioned conventional cooling device of Prior Art 1 or Prior Art 2, if the heat generating body generates heat due to an increase of the load thereof, even if no clogging actually occurs, it is erroneously judged that clogging has occurred. In addition, it is not necessary to monitor the temperature of the heat radiation structure for a long period of time taking the thermal time constant of the heat radiation structure into account.

What is claimed is:

1. A cooling device comprising:
a heat radiation structure having a plurality of radiation fin portions to be arranged on a heat generating body;
a cooling fan which generates an air flow which flows in a space between the radiation fin portions;
an electrode unit which is provided in the space and which is electrically insulated from the radiation fin portions;
a power supply source which applies a voltage between the heat radiation structure and the electrode unit;
a voltage detection unit which detects a voltage applied between the heat radiation structure and the electrode unit;
a current detection unit which detects a current which flows in a circuit formed by electrically and sequentially connecting at least the power supply source, the electrode unit, and the heat radiation structure;
an insulation resistance detection unit which calculates an insulation resistance between the heat radiation structure and the electrode unit based on the detection results of the voltage detection unit and the current detection unit; and
a comparison unit which compares the insulation resistance calculated by the insulation resistance detection unit with a predetermined threshold,
wherein, as a result of the comparison of the insulation resistance calculated by the insulation resistance detection unit and the predetermined threshold by the comparison unit, when the calculated insulation resistance is lower than the predetermined threshold, the cooling device is adapted to judge that the radiation fin portions have clogged.

2. The cooling device according to claim 1, further comprising a setting unit which sets the predetermined threshold, wherein the predetermined threshold set by the setting unit is rewritable.

* * * * *